United States Patent [19]

Triolo

[11] Patent Number: 4,503,150
[45] Date of Patent: Mar. 5, 1985

[54] POLYURETHANE FOAM AND A MICROBIOLOGICAL METABOLIZING SYSTEM

[75] Inventor: Rocco P. Triolo, Broomall, Pa.

[73] Assignee: Scotfoam Corporation, Eddystone, Pa.

[21] Appl. No.: 548,172

[22] Filed: Nov. 2, 1983

[51] Int. Cl.$^3$ .................. C12P 1/00; C12N 11/04; C08G 18/14

[52] U.S. Cl. .................. 435/41; 5.21/52; 5.21/159; 435/174; 435/182

[58] Field of Search ............... 521/159, 52, 914, 174; 435/41

[56] References Cited

U.S. PATENT DOCUMENTS

| | | | |
|---|---|---|---|
| 2,071,591 | 2/1937 | Tholin | 210/616 |
| 3,293,174 | 12/1966 | Robjohns | 210/150 |
| 3,779,906 | 12/1973 | Levin | 210/616 |
| 3,929,630 | 12/1975 | Smith | 210/617 |
| 4,005,010 | 1/1977 | Lunt | 210/150 |
| 4,055,490 | 10/1977 | Hasegawa et al. | 210/610 |
| 4,310,424 | 1/1982 | Fremont et al. | 210/393 |

FOREIGN PATENT DOCUMENTS

| | | |
|---|---|---|
| 1055169 | 5/1979 | Canada . |
| 2006181A | 5/1979 | United Kingdom . |

Primary Examiner—Herbert S. Cockeram
Attorney, Agent, or Firm—Connolly and Hutz

[57] ABSTRACT

The present invention provides a polyurethane foam having significantly improved longevity in a microbiological process in which the foam functions as a support medium for microorganism in a water system containing nutrients for the microorganisms. Also provided is a method of making said improved foam and an improved microbiological metabolizing (e.g., digestion) process employing said improved foam. The present invention is based upon the discovery that enhanced foam life in such a watery, abrasive environment is substantially enhanced if the polyurethane foam formulation has a urea/urethane ratio of less than about 5 and preferably a urethane index of about 100.

9 Claims, 1 Drawing Figure

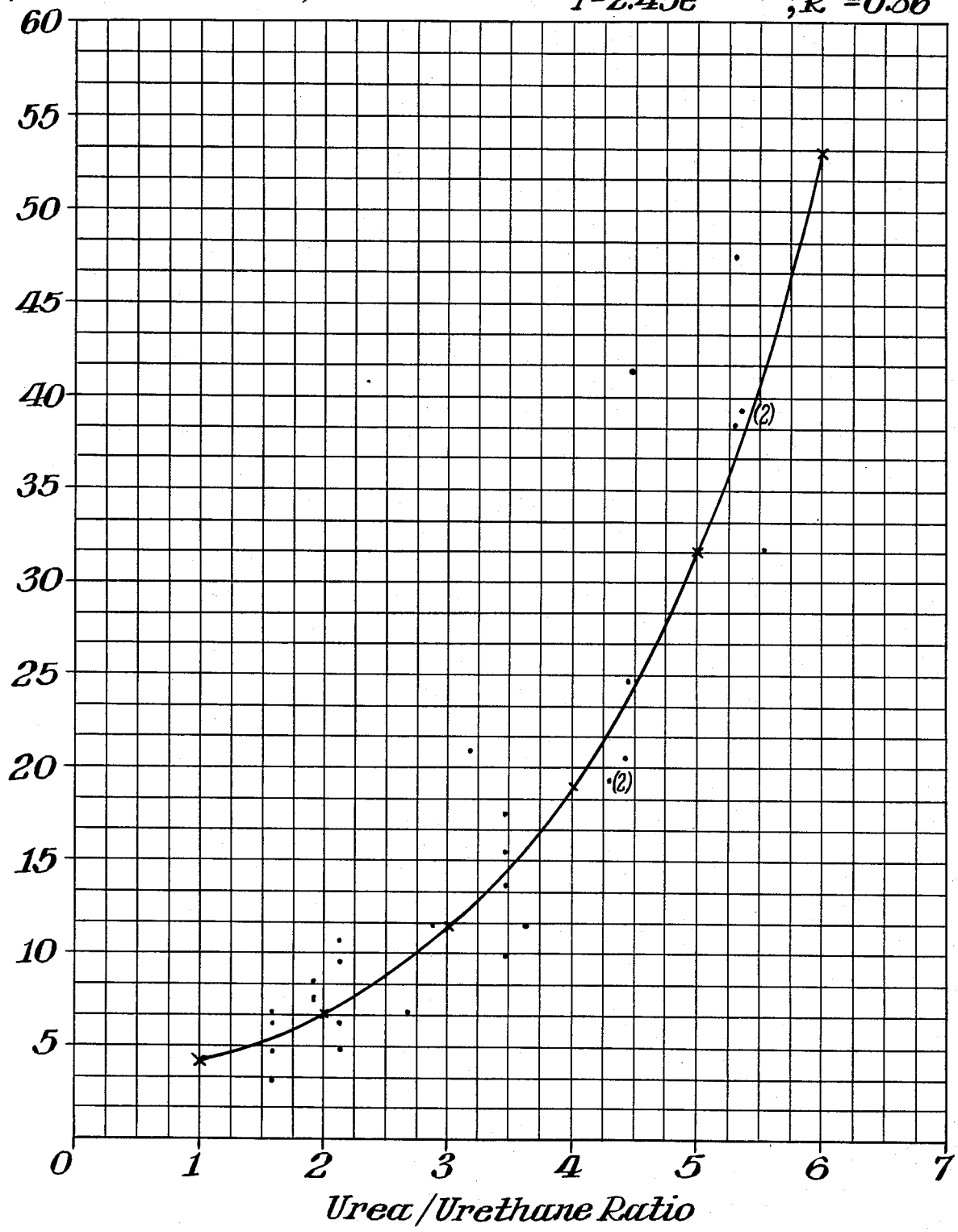

POLYURETHANE FOAM AND A MICROBIOLOGICAL METABOLIZING SYSTEM

BACKGROUND OF THE INVENTION

DESCRIPTION OF THE PRIOR ART

Polyurethane foams produced by the reaction of a polyether polyol with an isocyanate usually in the presence of a catalyst, surfactant and blowing agent are well known and generally referred to as polyether based polyurethane foams. Suitable reactants for producing polyurethane foam are well known and are generally disclosed in a monograph entitled "Polyurethanes, Chemistry and Technology" by J. H. Saunders and K. C. Firsch, 1962 published by Inter Science Publishers. Advances in polyurethane chemistry since the publication of the monograph are well known to those skilled in the art. Methods of producing polyether based polyurethane foam with flexible, semi-rigid or rigid properties are disclosed in U.S. Pat. No. 3,194,773 issued July 13, 1965 to F. Hostettler, entitled "Process of Making Polyurethane Foams." The Hostettler Patent discusses the effect of molecular weight and viscosity of polyether polyols upon the physical properties of the polyurethane foam produced from the polyether polyol.

Other patents that generally teach the characteristics of polyether polyols, isocyanates and other reactants with respect to polyurethane foams are U.S. Pat. No. 3,383,351 issued to P. Stamberger which concerns polymer polyols, and U.S. Pat. No. 3,454,505 issued to James Cross et al. which discuss various polyether polyols suitable for making polyurethanes.

Polyether polyols having a functionality of at least 2.0 are known to be suitable for producing flexible polyurethane foams and accordingly are suitable for practicing the present invention. The term "polyether polyol" is intended to include linear and branched polyethers (having ether linkages), and containing at least two hydroxyl groups. Preferred polyethers are the polyoxyalkylene polyols particularly the linear and branched poly(oxethylene)glycols, poly(oxypropylene)glycols and their co-polymers.

Polyether polyols have at least two active hydrogen atoms, (i.e., hydroxyl groups).

The term polyisocyanate refers to particularly those isocyanates which have previously been suggested for use in the preparation of polyurethane foams and includes di- and polyisocyanates and prepolymers of polyols and polyisocyanates having excess isocyanate groups available to react with additional polyol.

Chemically, the organic polyisocyanates which may be employed include both aromatic and aliphatic isocyanates. As used herein the term aliphatic isocyanate includes both aliphatic and alicyclic compounds as well as the aliphatic-like compounds—i.e., those which although they contain an aromatic ring, react as an aliphatic compound, due primarily to the fact that the isocyanate group is not attached directly to the ring.

The amount of polyisocyanate employed is frequently expressed by the term "Index" which refers to the ratio of the actual amount of isocyanate in the reaction mixture to the theoretical amount of isocyanate required for reaction with all the active hydrogen containing compounds present in the reaction mixture multiplied by 100. For most applications the Index is in the range of from about 70 to about 150, preferably from about 90 to about 130.

Catalysts that may be used to accelerate the polyol-polyisocyanate reaction include, for example, amines and metal salts the latter including both inorganic and organic salts. The catalyst may be either a single compound or a mixture of two or more compounds. It is especially preferred to employ, as the catalyst, an organotin salt or a tertiary amine.

The amount of catalyst employed may be varied over a wide range depending upon the formulation employed and the type of catalyst, all of which is well-known to those skilled in the art. For most applications the catalyst, either as a single compound or as a mixture of compounds, is employed in an amount equal to from about 0.01 to about 5.0 parts by weight per 100 parts by weight of polyol in the foam forming composition.

Polyurethanes are used in both the unfoamed and the so-called "foam" form. In general a foamed polyurethane is produced when low boiling liquids, gaseous blowing agents or inflatants are incorporated into or generated by the polyurethane foaming reactants. Often the heat of reaction causes the low boiling liquid or gaseous blowing agent to volatilize, thus foaming the composition. In some instances a technique generally referred to as frothing is employed in which case the boiling point of the blowing agent is chosen to be below room temperature. In this way the composition can be made to foam even before any substantial reaction between the polyol and the polyisocyanate reactants has occurred or before any heat is evolved.

Blowing agents which may be employed include, for example, water either alone or admixed with other components—e.g., as an aqueous solution of the catalyst. When water is employed it reacts with an excess of the polyisocyanate to generate carbon dioxide thereby resulting in a foam. Carboxyl containing compounds may also be included as a source of carbon dioxide.

Other useful blowing agents include the chlorinated and fluorinated alkanes having from 1 to about 3 carbon atoms such as the chlorofluorothanes; pentane; hexane; methylchloroform; butane; methylene chloride; difluoro-1,2-dichloroethylene and diethyl ether.

The amount of blowing agent employed can be varied over a wide range as is well-known to those skilled in the art depending primarily upon the density desired in the foam product. For most applications the blowing agent is employed in an amount equal to from about 2 to about 15 parts by weight per 100 parts by weight of polyol in the foam forming composition.

When blowing agents are included in or generated by the polyurethane reactants, there is also frequently included in the composition a surfactant type stabilizer the function of which is to control the amount and quality of the foamed polyurethane obtained. Without the stabilizer the foams may either collapse or contain very large uneven cells.

Representative surfactants which may be employed include:
  silicone compounds and silicone oil mixtures such as siloxaneoxyalkylene block copolymers;
  polyethylene glycol ethers of long chain alcohols;
  tertiary amine or alkylolamine salts of long chain alkyl acid sulfate esters, alkyl sulfonic esters and alkyl arylsufonic acids;
  compounds prepared by the sequential addition of propylene oxide and ethylene oxide to propylene glycol;
  castor oil sulfonate;
  ethylene oxide adducts of sorbitol;

mono-esters of long-chain fatty acids; and ethylene oxide adducts of alkyl phenols.

The amount of surfactant employed can be varied over a wide range depending, for example, on the foam-forming composition employed and the properties desired in the foam product. For most applications, the surfactant is employed in an amount equal to from about 0.1 to about 10 parts by weight per 100 parts by weight of the polyol in the foam-forming composition.

Support Structure

The polyurethane foam support structure for the active microorganism in the metabolic process must be flexible, open cell foam and have a controlled cell size to provide an appropriate host structure for the microorganisms.

The structural design of biological material support media, their materials of construction and the metabolic processes in which support medium can be utilized are well-known to those skilled in the present state of the art. A good example of a disclosure of metabolic processes employing support structures is contained in British Pat. No. 2,006,181B published as an application on May 2, 1979 and as a patent on May 19, 1982. The improved support structures of the present invention are particularly suitable for use in the processes disclosed in said British patent.

Canadian Pat. No. 1,055,169 entitled "Support Medium for Biological Treatment" is another good example of the disclosure of plastic support media from microorganisms in metabolic processes which discloses the use of foam plastic sheets as a support media for microorganisms in biological treatment process.

Another type of process utilizing a support structure which subjects the support structure to abrasion and flexing in a quite different manner than the above-mentioned processes is disclosed in U.S. Pat. No. 4,310,424 entitled "Apparatus and Method for Removing Suspended Solids from a Stream", issued Jan. 12, 1982 in which a cellular foam filter is the preferred support structure.

An early disclosure of an activated sludge sewerage treatment process using mobile support structures such as sponges is disclosed in U.S. Pat. No. 2,071,591 entitled "Sewerage Treatment", issued Feb. 23, 1937. Other examples of metabolic processes employing support structures, particularly sewerage or effluent treatment processes, employing different types of support structures and slightly different process configurations are disclosed in the following U.S. Pat. Nos. 3,293,174 issued Dec. 20, 1966 disclosing cubes of foam material such as polyurethane foam; 3,779,906 issued Dec. 18, 1973 discloses a different process configuration using plastic support structures; 3,929,630 issued Dec. 30, 1975 discloses a biochemical process employing a rigid porous foam substrate of absorbent silica; 4,005,010 discloses a support structure designed more like an open weave packing element made out of fibers which are woven into a porous net element.

Other disclosures of process employing a support medium in a biological treatment process are Canadian Pat. No. 1,055,169, which discloses a trickle bed type filter for biological treatment of sewerage or other aqueous effluent in which a mesh like material is used as a support medium and the preferred mesh like material is foamed plastics such as polyethylene foam.

U.S. Pat. No. 4,005,010 discloses a biological treatment process for aqueous fluids containing nutrients in which the support medium is individual plastic packing elements in a mesh bag.

U.S. Pat. No. 3,293,174 discloses the use of expanded polymeric materials (such as polyurethane foam) as a packing medium for improved aerated filter plants to provide a basis for a greater effective area of biologically active surface per unit volume of filter.

U.S. Pat. No. 3,779,906 also discloses a process employing a support medium to provide an attractive environment and surface area for the growth of sewage treatment microorganisms in which the support medium could be polyurethane foam.

Microbiological Digestion Process

Matabolic processes involve the growth of biological material in the presence of nutrients and consumes (metabolizes) nutrients (oxygen also if the process is aerobic) from the environment in which the biological growth is taking place. This basic biological phenomenon is used in many processes. When the organism is microscopic in size, the process is called a microbiological metabolic process.

Support medium for microscopic biological organisms has been employed to achieve higher active densities of the microorganism. Examples of the use of support media for microorganisms is disclosed in British Pat. No. 2,006,181B, the disclosure of which is incorporated herein by reference for its general disclosure of aerobic biological processes, equipment and support media. A particularly effective use of such a process is in the biological digestion of nutrients in a waste water treatment process generally known as activated sludge or secondary sludge treatment of sewerage waste. Sewerage treatment plant equipment needed to achieve a desired quantity of active biological organisms can be substantially reduced in size if the density of the active microorganisms (biological population per unit volume) is significantly increased. The biological support media provide a cellular support structure in which the microorganisms can grow and multiply in a suitable environment containing nutrients thereby achieving the desired higher density of active microorganisms.

A high surface area, porous cellular structure, such as reticulated polyurethane foam, has been found very suitable as a support structure for microbiological metabolic process such as a activated sludge waste treatment process in which nutrients are metabolized into carbon dioxide in the presence of oxygen by the growing and reproducing biological population. With appropriate cell size for the support structure, a high density of actively growing microorganisms can be achieved.

During the process, polyurethane foam support medium becomes partially filled with the expanding colony of microscopic biological organisms to achieve the high density. If the filling of the cells in the foam with microorganisms was permitted to continue unchecked, the expanding colony would choke off the source of nutrients within the support medium needed for the continued vitality of the growing colony of microorganisms. To prevent this, it is necessary to remove some of the accumulating active biomass from the support medium in order to keep open the pathways through the medium for replenishment of nutrients within support structure. With a flexible polyurethane foam support structure, this is readily achieved by removing the foam from the biological process and squeezing the foam to expel some of the active biomass. Returning the foam to the nutrient containing watery environment recycles active microorganisms in addition to recycling cleaned foam since all of the microorganisms are not removed in the cleaning or squeezing process steps.

When treating water containing nutrients by an active microbiological process employing polyurethane foam as a support medium, the polyurethane foam must undergo repeated cycles of being immersed in the nutrient rich water, accumulate active biomass, have biomass squeezed from the foam and return to the nutrient rich water for the process to begin over again. This repetitive squeezing and immersing of the polyurethane foam causes substantial abrasive degradation of the foam. Furthermore, the support structure and the nutrient rich water are usually agitated to provide uniformity of nutrients and oxygen if needed and support structures to enhance the flow of nutrients into cells of the support structure and biological wastes out of the cells. This agitation or mixing of the foam and the fluid being treated by the biological process also causes substantial abrasive degradation of the foam pieces functioning as a support structure.

An object of the present invention is to formulate a polyurethane foam having superior abrasion resistance in such water based microbiological digestion processes especially activated sludge waste treatment processes.

DESCRIPTION OF THE INVENTION

The improved polyurethane foam of the present invention, (high abrasion resistant polyurethane foam) is designed for use in small pieces in a vessel along with liquid containing nutrients, sometimes oxygen (or air), and a seed culture of desired microorganisms. Liquid containing the nutrients to be treated can be added continuously to the vessel and treated liquid effluent can be continuously moved from the vessel. During the biological digestion process, the vessel contents are continuously mixed thoroughly. If the biological process is aerobic, an oxygen source is continuously provided in order to maintain aerobic conditions throughout the vessel. Preferably the temperature is maintained between 20° C. and 35° C. Under such suitable conditions, the culture of microorganisms grow within the cells of the polyurethane support medium. Portions or pieces of the polyurethane support medium are removed usually continuously throughout the process. The pieces of polyurethane support medium removed from the vessel contain active microorganism culture within the cellular structure of the foam. The pieces of support medium are squeezed to remove some of the active culture within the cells and after squeezing, the polyurethane foam pieces are returned to the vessel. Preferably, the pieces still contain some of the microorganism culture for reinnoculation of the vessel with desired microorganisms.

Abrasion of the pieces of polyurethane support medium is significant during operation of the process due to the handling and squeezing of the pieces and also due to the continuous agitation of the vessel contents required to maintain uniform conditions within the vessel. Surprisingly, it has been discovered that the dominate mechanical abrasion experienced by the pieces is due to contact between the pieces during mixing within the vessel. Accordingly, improved abrasion resistance required a foam formulated to resist the repetitive contact between foam pieces during mixing and agitation rather than enhancing the strength or stiffness of the foam to resist repetative squeezing.

Based upon the observation of severe mechanical degradation of pieces of polyurethane foam due primarily to agitative interaction of the foam pieces rather than squeezing, (hereinafter referred to as "abrasion") it became an object of the present invention to formulate a polyurethane foam having superior abrasion resistance yet, retaining the desired pore size or cellular structure required for an effective microbiological support medium. Surprisingly, increasing the strength of polyurethane foam (usually measured in terms of compression deflection characteristics or tensile strength) did not necessarily increase the abrasion resistance of the foam.

It has been discovered that substantially different abrasion resistance can be possessed by polyurethane foams having similar densities or similar tensile strengths or similar elongation properties. The superior abrasion resistance provided by the present invention for polyurethane support medium in a microbiological digestion process is achieved when the polyurethane foam is made with a formulation having a urea to urethane ratio of less than about 5 and preferably with a urethane index of 100.

The superior abrasion resistance that the foam of the present invention possesses is resistance to a particular type of abrasion that surprisingly has been discovered to constitute the dominant form of abrasion encountered by pieces of support medium during continuous agitation in a large liquid filled vessel such as the process disclosed in said British Pat. No. 2,006,181B(?).

Urea/Urethane Ratio

The present invention defines polyurethane foam formulations in part, based upon the urea to urethane ratio. This ratio was discovered and found to correlate with abrasion resistance for polyurethane support medium. The ratio is based upon the theory that toluene diisocyanate (TDI) can be considered to react initially with the water present in the polyurethane foam formulation (urea reaction) and then with the polyol resin in the formulation (urethane reaction) because of the significant difference in reaction kinetics between the TDI-urea reaction and the TDI-urethane reaction. Accordingly, the urea to urethane ratio was devised to take into account different reaction kinetics. The ratio is based upon the fact that the toluene diisocyanate (TDI) reacts with water to produce urea groups while the TDI reaction with the polyol produces urethane groups.

The Urea/Urethane ratio is defined as the ratio of the equivalents of urea groups formed from the reaction of the isocyanate with water to the equivalents of urethane groups formed from the reaction of the isocyanate with the polyol. For example, urea/urethane ratio for Example 1A is calculated as follows:

| (a) | Equivalents of Urea |
| --- | --- |
| | $\dfrac{3.25 \text{ phr } H_2O}{9.0 \text{ E.W. } H_2O} = 0.3611$ Equivalents |
| (b) | Equivalents of Urethane |
| | $\dfrac{56.100}{58.1 \text{ (OH\#16-56)}} = 966.2$ E.W. 16-56 |
| | $\dfrac{100 \text{ phs 16-56}}{966.2 \text{ E.W. 16-56}} = 0.1035$ Equivalents |

-continued (c) Urea/Urethane Ratio $$\frac{0.3611 \text{ Eqs.}}{0.1035 \text{ Eqs.}} = 3.49$$

Urethane Index

Urethane index was the other important characteristic of the foam devised as an indicator of abrasion resistance. Urethane index is defined as: the actual amount of TDI available for reaction with the polyol divided by the stoichiometric amount of TDI required for reaction with the polyol. The Urethane Index does not exceed 100. If the actual amount of TDI available for reaction exceeds the theoretical amount required for reaction with the polyol, the excess TDI is considered to be consumed in cross-linking reactions such as biuret and allophonate formation.

It has been discovered that as the urea/urethane ratio increases, the abrasion resistance of the polyurethane foam decreases. It has also been discovered that a urethane index of 100 or higher is also desired for good abrasion resistance.

In polyurethane chemistry, an index (conventional index) is usually defined as: the actual quantity of TDI in the foam formulation divided by the stoichiometric quantity of TDI required for reaction with all active-hydrogen containing components (e.g., $H_2O$ and polyol) in the polyurethane foam formulation.

Accelerated Abrasion Resistance Tests

In order to determine abrasion resistance of polyurethane foam in a microbiological metabolic process an accelerated test was devised employing the following equipment and procedure.

Equipment: a ball mill jar having a volume of 2 liters and a diameter of 21.25 centimeters; burundum cylinders about 1 centimeter in diameter and about 2 centimeters long (ceramic grinding media); a sieve (30 mesh U.S. standard series); and a roller mill capable of rotating the ball mill jar at about 83 revolutions per minute.

Procedure: 183 samples of polyurethane foam formulation to be tested (1.26 centimeter cubes each) are weighed and placed in the ball mill jar. One liter of water and 750 grams of burundum ceramic cylinders are added to the ball mill jar and the jar is secured with a cap. The ball mill jar is rotated at about 83 revolutions per minute on the roller mill for 24 hours. The contents of the ball mill jar are drained through the 30 mesh sieve. The material retained on the sieve is rinsed with water to remove any residue. The foam pieces are separated from the burundum ceramic cylinders, squeezed between paper towels to remove excess water, dried for one hour in an oven at 110° C. and then weighed. An abrasion index is given as percent weight loss per unit time, and is calculated as the percent weight loss of the foam cubes divided by the test time in hours. The improved foams of the present invention exhibit abrasion resistance indices of less than 0.25%/hr under 144 hour tests.

EXAMPLE 1

Four polyurethane foam samples were prepared and designated 1a, 1b, 1c and 1d, each having a urethane index of 100. The foam formulations for each foam sample were kept as identical as possible in order to obtain a fair comparison of abrasion resistance at different urea to urethane indexes. More TDI and water were used in the formulation for foam sample 1b than 1a in order to raise the urea/urethane index while in order to achive the same degree of blowing (density and pore size), some Freon was used in the formulations for foam 1a and 1c. A similar comparison exists between foam samples 1c and 1d. The urea to urethane ratio was 3.49 for foams 1a and 1c, 5.37 for foam 1b and 4.30 for foam 1d. The foam formulations are given in Table 1.

Formulation Procedures

The foam samples were made as handmixes in the laboratory. All components, with the exception of TDI, are weighed into a single container and premixed 10-20 seconds. While continuing to mix, the appropriate amount of TDI is added and mixing continued another 5-10 seconds. Mixing is stopped and the pre-foam mix is transferred to an open, cardboard box (mold). The mixture is allowed to free rise and stand until the polymer sets (usually 5 to 10 minutes). The foam is cured one hour at 110° C., allowed to stand 24 hours, reticulated and then prepared for abrasion resistance testing.

TABLE I

| | Sample No. | | | |
|---|---|---|---|---|
| | 1A | 1B | 1C | 1D |
| FORMULATION (Parts) | | | | |
| Niax 16-56 Polyol | 100 | 100 | 100 | 100 |
| L6202 | 1.0 | 1.2 | 1.0 | 1.0 |
| C-6 | 0.4 | 0.6 | 0.4 | 0.9 |
| Dabco 33 LV | 0.6 | 0.4 | 0.6 | 0.6 |
| C-124 | 0.7 | 0.7 | 0.7 | 0.7 |
| $H_2O$ | 3.25 | 5.0 | 3.25 | 4.0 |
| Freon-11 | 10 | — | 5 | — |
| TDI | 41.43 | 57.35 | 41.43 | 48.68 |
| Index | 102 | 100 | 102 | 102 |
| Urethane Index | 100 | 100 | 100 | 100 |
| Urea/Urethane | 3.49 | 5.37 | 3.49 | 4.30 |
| Crosslinking | .0115 | 0 | .0115 | .0115 |
| RESULTS | | | | |
| P.P.I. | 37 | 40 | 40 | 45 |
| Density (lbs./ft.$^3$) | 1.34 | 1.33 | 1.57 | 1.59 |
| Tensile | 12.8 | 32.5 | 14.2 | 27.1 |
| % Elongation | 349 | 358 | 348 | 389 |
| Tear | 3.0 | 3.9 | 3.1 | 4.1 |
| Abrasion (% wt. loss) | | | | |
| After 72 Hours | 8.1 | 22.3 | 6.8 | 9.4 |
| After 144 Hours | 17.5 | 39.2 | 13.7 | 19.3 |

As can be seen by a comparison of the foam properties for foam samples 1a and 1b, essentially identical densities and pore sizes were obtained for the two foams. The samples were tested for abrasion resistance using the above procedure. The results are given in Table 1. Surprisingly, sample 1b has dramatically higher weight loss (lower abrasion resistance) than samples 1a, 1c and 1d. However, sample 1b has about the same density as sample 1a (equivalent amounts of polymer in the foam structure) and was stronger than samples 1a, 1b and 1d (higher tensile strength, tear strength and elasticity i.e., % elongation which properties under prior conventional reasoning suggest a stronger, more abrasion resistant foam). A comparison of foam sample 1c with 1d supports the surprising conclusion that urea to urethane ratio for the polyurethane formulation has a tremendous influence upon the abrasion resistance of the resulting polyurethane foam. Traditional adjustments to polyurethane foam formulations to obtain denser or stronger foams are not as significant in controlling abrasion resistance and can actually lower the abrasion resistance of the foam. This surprising conclusion is supported by samples 1c and 1d that have equivalent densities. Sample 1d is less abrasion resistant than sample 1c although stronger in such traditional measurements of strength as tensile strength, tear strength (e.g. shear) and elasticity.

It is concluded from the above examples that neither density nor pore size by themselves determine abrasion resistance but surprisingly, the urea to urethane index is a key factor in the foam formulation to produce a highly abrasion resistant polyurethane foam. Likewise, the urethane index in all of the samples was 100. If the urethane index was lower, abrasion resistance would be also lower for all of the samples.

EXAMPLE 2

Five samples of polyurethane foam were produced and designated as samples 2a, 2b, 2c, 2d and 2e. The samples were tested for abrasion resistance using the above procedure. The formulations for each sample were adjusted in order to obtain comparative sample pairs having similar densities (2a and 2e), similar tensile strengths (2a and 2d) and similar pore sizes (2b and 2e). The formulations, physical properties of the samples, and test results are given in Table II. Samples 2a and 2e each had a density of 2.3 pounds per cubic foot (0.037 gm/cc). However, the abrasion resistance of foam sample 2a was substantially higher than the abrasion resistance of foam sample 2e. Foam samples 2a and 2d had the same tensile strength, although sample 2a had significantly higher abrasion resistance. Sample 2b has a pore size comparable to sample 2e but significantly higher abrasion resistance than sample 2e. The strongest foams in terms of tensile strength (2d and 2e) had the worst abrasion resistance.

In order to produce samples 2a, b, c, d and e with foam formulations as identical as possible, while still varying the urea to urethane index, it was necessary to change the foaming conditions under which the foam forming chemicals reacted. Foam samples 2a and 2d were produced under free rising conditions (atmospheric pressure), foam samples 2b and 2c were produced under a reduced pressure (vacuum) to obtain low densities comparable to foam sample 2d, while foam sample 2e was foamed under slightly elevated pressure in order to achieve a density as high as foam sample 2a.

Formulation Procedures

In samples 2A, 2B, 2C, 2D and 2E, density was also controlled by external pressure during foaming. All foaming was done on a laboratory scale (M3V) foam machine as follows:

1. Foam making procedure at atmospheric pressure—all components were accurately and simultaneously metered into a central mixing chamber where the foam reactants were mixed. Then the prefoam mix was dispensed into a container. The container was a pressure vessel with a clear plexiglass top fitted directly to the foam machine head. The vessel had valving to allow glass to be introduced, vented or exhausted. The vessel was sized to accommodate 5 gallon plastic bags as a removable foam mold.

2. Foaming under pressure—the same procedure as atmospheric foaming was employed except a predetermined amount of foam reactants was poured into the sealed pressure vessel and allowed to rise until the gases ($CO_2$) and heat evolved from the reactions generated a pressure of approximately 20-21 psig. This pressure restrained the rising foam volume resulting in almost doubling of the expected free-rise density.

3. Foaming under vacuum—the same procedure as atmospheric pressure foaming was employed except a predetermined weight of foam reactants was poured into the pressure vessel under a vacuum of 17.5″ Hg. The foam was allowed to expand under vacuum to a height (volume) calculated to approximately yield one-half the free-rise density. At this point the vacuum pump was cut off from the system, but vacuum was maintained for one (1) hour. After this period, the vacuum was slowly broken, pressures equilibrated and the sample removed for evaluation.

TABLE II

| | Sample No. | | | | |
|---|---|---|---|---|---|
| | 2A | 2B | 2C | 2D | 2E |
| FORMULATION | | | | | |
| Niax 15-16 Polyol | 100 | 100 | 100 | 100 | 100 |
| L6202 | 1.0 | 1.0 | 1.0 | 1.0 | 1.0 |
| C-9 | 0.8 | 0.8 | 0.5 | 0.8 | 0.8 |
| C-124 | 1.0 | 1.0 | 1.0 | 1.0 | 1.0 |
| $H_2O$ | 1.8 | 1.8 | 1.8 | 5.0 | 5.0 |
| TDI | 29.1 | 29.1 | 29.1 | 63.2 | 63.2 |
| Index | 110 | 110 | 110 | 110 | 110 |
| Foaming Conditions | Free Rise | Vacuum | Vacuum | Free Rise | Pressure |
| Urethane Index | 100 | 100 | 100 | 100 | 100 |
| Urea/Urethane | 1.913 | 1.913 | 1.913 | 5.314 | 5.314 |
| Crosslinking | .0298 | .0298 | .0298 | .0661 | .0661 |
| RESULTS | | | | | |
| P.P.I. | 68 | 58 | 45 | 42 | 55 |
| Density | 2.3 | 1.6 | 1.2 | 1.2 | 2.3 |
| Tensile | 21.3 | 15.6 | 6.4 | 21.2 | 47.0 |
| % Elongation | 381 | 387 | 309 | 283 | 259 |
| After 72 Hours | 4.8 | 3.8 | 3.6 | 32.0 | 32.2 |
| After 144 Hours | 8.5 | 7.7 | 7.6 | 47.4 | 38.5 |

It has been concluded from a comparison of samples 2a, b, c, d and e that foams of identical density can have significantly different abrasion resistance depending upon the urea to urethane index and likewise foams of identical tensile strength can differ significantly in abrasion resistance depending upon the urea to urethane index. Similarly, foams having comparable cell structure (cell size) can differ significantly in abrasion resistance.

Although samples 2d and 2e had lower percent elongation than samples 2a, 2b or 2c surprisingly, the most dramatic difference in elongation is between samples 2b and 2c yet, this difference in elongation did not correlate well with improvement in abrasion resistance. It can be generally observed from the data that higher elongation (stretches more easily) usually provides a more abrasion resistant foam.

Foam Reactants Identified in Table I

1. Niax Polyol 16–56 is a trademark of Union Carbide for a 3000 molecular weight, trifunctional polyether polyol resin (made by Union Carbide). It is a reaction product of glycerine, ethylene oxide and propylene oxide. It contains 8 to 10% internal ethylene oxide.
2. L6202 is a trademark for a hydrolyzable silicone surfactant for use in the manufacture of flexible polyether foam and made by Union Carbide.
3. Fomrez C-9 is a trademark for a catalyst consisting of one part of stannous octoate carried in 5 parts dioctylphthalate and made by Witco Chemical Company.

4. Niax Catalyst C-124 is a trademark for a catalyst consisting of one part of bis(2-dimethylaminoethyl)ether carried in 6 parts dipropylene glycol. Made by Union Carbide.
5. Fomrez C-6 is a trademark for a catalyst consisting of one part of stannous octoate carried in 2 parts dioctylphthalate. Made by Witco Chemical Company.
6. Dabco 33LV stands for a catalyst consisting of one part of Dabco carried in 2 parts of dipropylene glycol. Dabco is triethylene diamine, made by Air Products.
7. Freon-11 is a trademark for a low boiling point blowing agent, trichloromonofluoromethane made by Union Carbide.
8. TDI stands for toluene diisocyanate commercially available as an isomer mixture.

ADDITIONAL EXAMPLES

Many foam samples were prepared with different urea to urethane ratios and at different urethane indexes and each sample was tested for abrasion resistance using the procedure described above and an abrasion test time of 144 hours. The percent weight loss of the foam sample was plotted against the urea to urethane ratio and the data points appear in the FIGURE. A regression analysis of the data was performed to determine the mathematical formula defining the relationship between abrasion resistance and urea to urethane ratio which best fits the data.

Although reasonably good correlations were obtained with a number of mathematical formulae (e.g., straight line, exponential and power curves), the exponential curve appears to provide the best fit to the data. The exponential curve generated was as follows:

$$Y = 2.45 e^{(0.51)(x)} \qquad R^2 = 0.86$$

where Y is the abrasion resistance using the procedure described above and an abrasion test time of 144 hours and X is the urea/urethane ratio as previously defined. The line shown in FIG. 1 is the plot of the mathematical formula calculated by the regression analysis. As can be seen from the data, the highest abrasion resistance is achieved with foams having lower urea to urethane ratios and the data points suggests a separation in the abrasion resistance between foams having a urea to urethane ratio less than about 5 versus foams having higher urea to urethane ratios. Although urea to urethane ratio is not the sole predictor of abrasion resistance, density, pore size and elongation also affect abrasion resistance. The surprising discovery is that in addition when any of the traditional indicators of polyurethane foam strength are the same between two foams, the foam with the lower urea to urethane ratio has surprisingly better abrasion resistance. Conversely, abrasion resistance is improved when the foam formulation is modified to lower the urea/urethane ration.

The best mode presently contemplated for practicing the present invention is to select a polyurethane foam formulation employing conventional chemical reactants to achieve a polyurethane foam having good hydrolytic stability and flexibility in accordance with known art but to adjust the foam formulation so selected to have a urea to urethane ratio less than about 5 and preferably between 1 and 4 and also for the foam formulation to have a urethane index of 100. Polyurethane foam is preferably reticulated (dewindowed) and used in particles of generally cubic or spherical shape of about one to give centimeters in diameter or on a side. Foam preferably has a density of between 1 and 5 lbs/ft$^3$ (0.016 to 0.080 gm/cc) and a pore size of from 10 to 100 pores per inch (PPI) of foam surface.

A microbiological metabolic process is preferably performed employing the above described preferred foam in a large vessel into which the nutrient containing water is fed under suitable temperature and oxygen (or lack of oxygen) conditions for growth of the desired microorganism in the vessel. The vessel contents are preferably agitated and suitable growth conditions maintained in the vessel throughout the process. Under such conditions, the cells in the foam become loaded with colonies of the microorganism. Such loaded foam pieces (support structure) are removed from the vessel microorganism removed as by squeezing and the foam returned to the vessel. Preferably, steady-state conditions are maintained by continuously adding the nutrient stream, removing treated liquid and removing foam, squeezing and returning foam to the vessel.

I claim:
1. A flexible, open cell, polyurethane foam having improved abrasion resistance produced by the process of reacting conventional polyurethane foam-forming chemicals including a polyol resin of a type suitable for making flexible polyurethane foam, an isocyanate and water in the presence of catalyst and a surfactant and in which the proportions of polyol, water and isocyanate reacted to produce said foam correspond to a urea to urethane ratio of less than about 5.

2. A flexible, open cell, reticulated polyurethane foam having improved abrasion resistance and produced from polyurethane foam-forming reactants having a urea to urethane ratio of less than about 5.

3. The foam of claims 1 or 2 having a density of from 1 to 5, pounds per cubic foot (0.016 to 0.080 gm/cc), a pore size of from 10 to 100 pores per inch of and a urethane index of from about 90 to about 100.

4. Process of producing flexible, open cell, polyurethane foam having improved abrasion resistance comprising reacting a polyether polyol resin for making flexible polyurethane foam, isocyanate, water and a surfactant in the presence of a catalyst wherein the proportion of the reactants correspond to a urea to urethane ratio of less than about 5.

5. An microbiological support structure comprising a flexible, open cell, reticulated, polyurethane foam having a urea to urethane ratio of less than 5, an abrasion resistance index of less than 0.25% weight loss per hour, a density of from 1 to 5 pounds per cubic foot (0.016 to 0.080 gm/cc), a pore size of from 10 to 100 pores per inch and a urethane index of from about 90 to 100.

6. The polyurethane foam of claims 1, 2 or 3 in which the proportion of foam-forming reactants correspond to a urethane index of about 90 to about 100.

7. The polyurethane foam of claims 1, 2 or 3 in which the urea to urethane ratio is between 1.5 and 4.

8. A flexible polyurethane foam having improved abrasion resistance and produced by
reacting a polyurethane foam composition comprising polyurethane foam-forming reactants for producing a polyurethane foam having good hydrolytic stability and flexibility
wherein the proportion of the polyurethane foam-forming reactants correspond to a urea to urethane index of less than about 5.

9. In an improved microbiological metabolic process which comprises agitating a generally cellular support structure for microbiological organisms in an aqueous medium containing microbiological organisms and nutrients for said organisms, the improvement which comprising employing a cellular support structure having cells predominantly in the size range of from 10 cells per inch to 100 cells per inch and being sufficiently open to readily permit flow of the aqueous medium into and out of the cells and said structure comprising a flexible, abrasion-resistant reticulated polyurethane foam produced from a proportion of polyurethane foam forming reactants which provide a urea to urethane ratio of less than 5.

* * * * *